United States Patent [19]

Schaper et al.

[11] Patent Number: 4,719,043

[45] Date of Patent: Jan. 12, 1988

[54] ISOMERIC 1-ALKYL/ALKENYL-2,2,4(2,4,4)-TRIMETHYL CYCLOPENTAN-1-OLS AS PERFUMES

[75] Inventors: Ulf-Armin Schaper, Krefeld; Klaus Bruns, Krefeld-Traar; Siegfried Bloesl, Schwaebisch-Gmuend; Benno Streschnak, Krefeld, all of Fed. Rep. of Germany

[73] Assignee: Henkel Kommanditgesellschaft auf Aktien, Duesseldorf, Fed. Rep. of Germany

[21] Appl. No.: 28,289

[22] Filed: Mar. 20, 1987

[30] Foreign Application Priority Data

Mar. 21, 1986 [DE] Fed. Rep. of Germany ....... 3609524

[51] Int. Cl.$^4$ .......................... A61K 7/46; C07C 35/08
[52] U.S. Cl. .......................................... 512/8; 568/838
[58] Field of Search ..................... 568/838; 252/522 R

[56] References Cited

U.S. PATENT DOCUMENTS 4,302,363  11/1981  Bruns et al. ..................... 252/522

FOREIGN PATENT DOCUMENTS 200829  2/1956  Australia ........................... 568/874
21356   2/1983  European Pat. Off. .

OTHER PUBLICATIONS

Mitsui et al, "Chemistry and Industry".
Chaikin et al, "J. Amer. Chem. Soc.", vol. 71, (1949), pp. 122–125.
J. S. Jellinek, "Parfumieren von Produkten", pp. 100–101, Dr. A. H. Huthig Verlag (pub.), Heidelberg, 1976.
Min-Hon Rei, J. Org. Chem. 43, 2173 (1978).

*Primary Examiner*—Werren B. Lone
*Attorney, Agent, or Firm*—Ernest G. Szoke; Henry E. Millson, Jr.; Mark A. Greenfield

[57] ABSTRACT

The invention relates to isomeric 1-alkyl/alkenyl-2,2,4(2,4,4)-trimethyl cyclopentan-1-ols corresponding to general formulae I a/b below

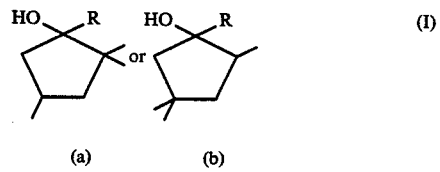

in which R is $C_{2-5}$ alkyl or a $C_{3-5}$ alkenyl; the use of compounds of the same formula in which R is $C_{1-5}$ alkyl or $C_{2-5}$ alkenyl as perfumes in compositions containing active chlorine or capable of generating active chlorine; and methods for their preparation.

25 Claims, No Drawings

ISOMERIC 1-ALKYL/ALKENYL-2,2,4(2,4,4)-TRIMETHYL CYCLOPENTAN-1-OLS AS PERFUMES

BACKGROUND OF THE INVENTION

1. Field of the Invention

This invention relates to isomeric 1-alkyl/alkenyl-2,2,4(2,4,4)-trimethyl cyclopentan-1-ols, to a process for their production, and to their use as perfumes in compositions containing active chlorine.

2. Statement of Related Art

In many consumer goods, for example in body-care preparations or fabric softeners, problems regarding the stability of the perfumes used are unknown. By contrast, compositions containing active chlorine, such as dishwashing detergents and/or scouring preparations and the like, destroy most perfumes so that perfuming with the desired fragrance notes is no longer possible (cf. J. S. Jellinek: "Parfumieren von Produkten", pp. 100–101, Dr. Alfred Huthig Verlag (pub.), Heidelberg, 1976). In addition, destruction of the perfumes is often accompanied by an undesirably high reduction of the active chlorine content.

DESCRIPTION OF THE INVENTION

Other than in the operating examples, or where otherwise indicated, all numbers expressing quantities of ingredients or reaction conditions used herein are to be understood as modified in all instances by the term "about".

The present invention provides perfumes which are stable in compositions containing active chlorine, methods for their preparation, and methods for their use.

It has surprisingly been found that no stability problems arise where one or more isomeric 1-alkyl/alkenyl-2,2,4(2,4,4)-trimethyl cyclopentan-1-ols corresponding to general formulae I a/b below

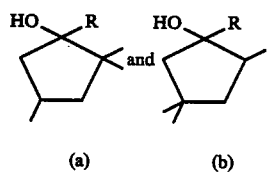

in which R is a $C_{1-5}$ alkyl or a $C_{2-5}$ alkenyl are used as perfumes in mixtures containing active chlorine or capable of generating active chlorine upon storage, exposure to moisture or heat, etc.

The present invention also relates to the above isomeric 1-alkyl/alkenyl-2,2,4(2,4,4)-trimethyl cyclopentan-1-ols per se when R is a $C_{2-5}$ alkyl or a $C_{3-5}$ alkenyl, since these compounds are believed to be novel.

Isomeric cyclopentan-1-ols corresponding to general formulae I a/b, in which R is ethyl, n-butyl or allyl, are particularly preferred.

The present invention also relates to a process for the preparation of the above isomeric cyclopentan-1-ols corresponding to general formulae I a/b by reaction of isomeric 2,2,4(2,4,4)-trimethyl cyclopentanones corresponding to general formulae II a/b below with Grignard compounds of the formula R—MgX, in which R is $C_{2-5}$ alkyl or $C_{3-5}$ alkenyl, preferably ethyl, n-butyl or allyl, and X is a halogen atom; in ether at around 36° C. The salts formed are converted into the isomeric cyclopentan-1-ols corresponding to general formulae I a/b by subsequent hydrolysis.

Isomeric cyclopentan-1-ols corresponding to general formulae I a/b, in which R is $C_{1-5}$ alkyl or $C_{2-5}$ alkenyl, preferably methyl, ethyl, n-butyl, vinyl or allyl, are preferably used as perfumes in mixtures containing active chlorine, or capable of generating active chlorine.

The cyclopentan-1-ols: 1,cis-2,4,4-; and 1,trans-2,4,4-tetramethyl chyclopentan-1-ol; and the isomeric 1-vinyl-2,2,4(2,4,4)-trimethyl cyclopentan-1-ol; have already been described in the literature. The two methyl compounds were prepared by Min-Hon Rei [J. Org. Chem. 43, 2173 (1978)] during his studies of the reactions of methyl-substituted cyclopentanones with lithium aluminum hydride and methyl lithium by reaction of 2,4,4-trimethyl cyclopentan-1-one with methyl lithium in ether at 0° C. The vinyl-substituted cyclopentanol is described in U.S. Pat. No. 4,302,363 (and corresponding European patent 21,356) as a preliminary stage in the preparation of 4(5)-acetyl-7,7,9(7,9,9)-trimethyl bicyclo-(4.3.0)-non-1-ene. It is prepared by reaction of 2,2,4(2,4,4)-trimethyl cyclopentanone with vinyl magnesium bromide in tetrahydrofuran for 12 hours at around 66° C.

However, neither of these two literature references discloses any information on the odor of the cyclopentanols obtained or on their stability with respect to mixtures containing active chlorine.

The preparation of the isomeric cyclopentanols corresponding to general formulae I a/b was effected by a synthesis process generally known in organic chemistry: isomeric 2,2,4(2,4,4)-trimethyl cyclopentanone was reacted with an excess of around 10 to 15 mol% (based on the alkylhalide used) of the corresponding alkyl or alkenyl magnesium halide in ether at around 36° C. The reaction mixture was then cooled to around 0° C. and hydrolyzed.

The isomeric cyclopentan-1-ols corresponding to general formulae I a/b, particularly where R was methyl ethyl, n-butyl, vinyl or allyl, were subjected to a storage test. It was surprisingly found that, even after 1 year at room temperature, no changes in odor occurred either in liquid or in solid mixtures containing active chlorine.

EXAMPLES

General procedure for the preparation of 1-alkyl/alkenyl-2,2,4(2,4,4)-trimethyl cyclopentan-1-ols In a thoroughly heated apparatus, 20 ml of a solution of 0.5 mol alkylhalide in 150 ml ether were added dropwise to 0.5 mol magnesium chips in 50 ml anhydrous ether. When the Grignard reagent began to form, the rest of the alkylhalide solution was added quickly so that the either boiled gently. On completion of the addition, the reaction mixture was heated under reflux for about another 30 minutes.

0.45 mol 2,2,4(2,4,4)-trimethyl cyclopentanone (isomer ratio 2,2,4:2,4,4=61:39) in 100 ml ether was added dropwise with stirring to the cooled Grignard solution, followed by stirring under reflux for about 30 minutes.

For working up, the reaction mixture was cooled to 0° C. and poured carefully into a cold saturated NH4Cl-solution (approx. 300 ml). The ether phase was then separated off and the aqueous phase extracted twice with 80 ml ether. The combined ethereal phases were washed with saturated sodium hydrogen carbonate and sodium chloride solution. After drying with sodium sulfate and evaporation of the solvent, the residue was distilled in vacuo. Some specific compounds produced were:

(A) 1,2,2,4(1,2,4,4)-tetramethyl cyclopentan-1-ol
Bp. 90° C./70 mbar, $n_D^{20} = 1.4476$
odor: camphory, borneol-like, rosemary note.

(B) 1-ethyl-2,2,4(2,4,4)-trimethyl cyclopentan-1-ol
Bp. 64° C./12 mbar, $n_D^{20} = 1.4520$
odor: camphory, woody, pyrethrum-, anthoxan-note (C) 1-n-butyl-2,2,4(2,4,4)-trimethyl cyclopentan-1-ol
Bp. 80° C./39 mbar, $n_D^{20} = 1.4527$
odor: earthy, woody, geosmine note (D) 1-vinyl-2,2,4(2,4,4)-trimethyl cyclopentan-1-ol
Bp. 67° C./19 mbar, $n_D^{20} = 1.4601$
odor- camphor-, verdol-note (E) 1-allyl-2,2,4(2,4,4)-trimethyl cyclopentan-1-ol
Bp. 114° C./117 mbar, $n_D^{20} = 1.4631$
odor: patchone- , herb-note.

Typical Bouquet for Liquid and Solid Compositions Containing Active Chlorine such as used in Storage Tests 30 parts by weight camphor (synthetic)
20 parts by weight musk xylene
100 parts by weight 4-(4-methyl-3-penten-1-yl)-3-cyclohexene-1-carbaldehyde
140 parts by weight isobornyl acetate
100 parts by weight eucalyptol
10 parts by weight clove leaf oil
200 parts by weight 1,2,2,4(1,2,4,4)-tetramethyl cyclopentan-1-ol [PERFUME]
180 parts by weight dihydromyrcenol
20 parts by weight 2,6-dimethylheptan-2-ol
100 parts by weight rosemary oil (span.)
100 parts by weight dipropylene glycol The above bouquet, or one prepared with similar ingredients well known in the art, may be employed in any conventional or new composition which contains active chlorine, or is capable of releasing active chlorine upon storage and/or exposure to moisture. The formulations of such compositions do not affect the perfumes of this invention except as disclosed herein, and therefore do not form a part of this invention. The compositions may comprise any dishwashing, laundry, commercial or household detergent and/or scouring preparation, to which the perfumes of this invention are added. The amount of addition will vary with the composition ingredients, amount of free chlorine, etc., but must be in at least a perfume-effective amount. The addition may be in any order of ingredients, and may be of the perfume per se or of a conventional bouquet of the type abovementioned. There are no limitations as to physical conditions of the addition or the compositions, other than those already known in the art. The compositions with the added perfumes are considered novel.

We claim:

1. Isomeric 1-alkyl/alkenyl-2,2,4(2,4,4)-trimethyl cyclopentan-1-ols corresponding to general formulae I a/b below

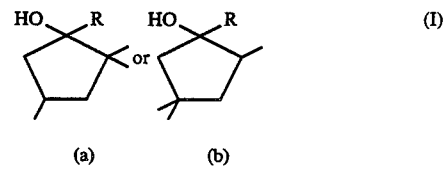

in which R is a $C_{2-5}$ alkyl or a $C_{3-5}$ alkenyl.

2. The isomeric cyclopentan-1-ols of claim 1, in which R is ethyl, n-butyl or allyl.

3. A process for preparing the isomeric cyclopentan-1-ols of claim 1 comprising reacting an isomeric 2,2,4(2,4,4)-trimethyl cyclopentanone corresponding to general formulae II a/b

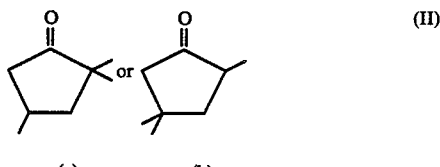

with Grignard compounds of the formula R-MgX, in which R is $C_{2-5}$ alkyl or $C_{3-5}$ alkenyl, and X is a halogen atom, in ether at around 36° C.; and converting the salts formed into the isomeric cyclopentan-1-ols corresponding to general formulae I a/b by subsequent hydrolysis.

4. A process for preparing the isomeric cyclopentan-1-ols of claim 1 comprising reacting an isomeric 2,2,4(2,4,4)-trimethyl cyclopentanone corresponding to general formulae II a/b

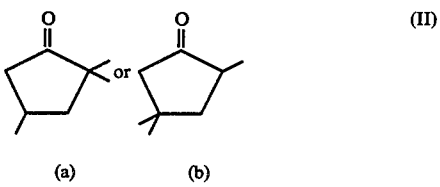

with Grignard compounds of the formula R—MgX, in which R is ethyl, n-butyl, or allyl, and X is a halogen atom, in ether at around 36° C.; and converting the salts formed into the isomeric cyclopentan-1-ols corresponding to general formulae I a/b by subsequent hydrolysis.

5. A method for perfuming a composition containing active chlorine, or capable of generating active chlorine, comprising incorporating within said composition at least a perfume-effective amount of at least one compound of the formula

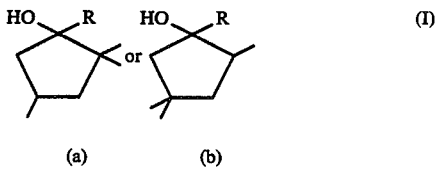

in which R is a $C_{1-5}$ alkyl or $C_{2-5}$ alkenyl.

6. The method of claim 5 wherein said compound is 1,2,2-4(1,2,4,4)-tetramethyl cyclopentan-1-ol.

7. The method of claim 5 wherein said compound is 1-ethyl-2,2,4(2,4,4)-trimethyl cyclopentan-1-ol.

8. The method of claim 5 wherein said compound is 1-n-butyl-2,2,4(2,4,4)-trimethyl cyclopentan-1-ol.

9. The method of claim 5 wherein said compound is 1-vinyl-2,2,4(2,4,4)-trimethyl cyclopentan-1-ol.

10. The method of claim 5 wherein said compound is 1-allyl-2,2,4(2,4,4)-trimethyl cyclopentan-1-ol.

11. The method of claim 5 wherein said composition is a detergent and/or scouring preparation.

12. A perfumed composition obtained by the method of claim 5.

13. A perfumed composition obtained by the method of claim 6.

14. A perfumred composition obtained by the method of claim 7.

15. A perfumed composition obtained by the method of claim 8.

16. A perfumed composition obtained by the method of claim 9.

17. A perfumed composition obtained by the method of claim 10.

18. A perfumed composition obtained by the method of claim 11.

19. In a detergent and/or scouring composition containing active chlorine and/or which is capable of generating active chlorine, the improvement wherein a perfumeeffective amount of at least one compound is added, said compound being of the formula:

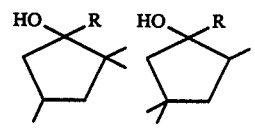

(a)  (b)

(I)

wherein R is a $C_{1-5}$ alkyl or a $C_{2-5}$ alkenyl.

20. The composition of claim 19 wherein said compound is 1,2,2,4(1,2,4,4)-tetramethyl cyclopentan-1-ol.

21. The composition of claim 19 wherein said compound is 1-ethyl-2,2,4(2,4,4)-trimethyl cyclopentan-1-ol.

22. The composition of claim 19 wherein said compound is 1-n-butyl-2,2,4(2,4,4)-trimethyl cyclopentan-1-ol.

23. The composition of claim 19 wherein said compound is 1-vinyl-2,2,4(2,4,4)-trimethyl cyclopentan-1-ol.

24. The composition of claim 19 wherein said compound is 1-allyl-2,2,4(2,4,4)-trimethyl cyclopentan-1-ol.

25. The composition of claim 19 wherein R is methyl, ethyl, n-butyl, vinyl, or allyl.

* * * * *